United States Patent
Moro et al.

(10) Patent No.: US 10,265,420 B2
(45) Date of Patent: *Apr. 23, 2019

(54) SOLID COMPOSITION FOR THE ORAL ADMINISTRATION OF DYES AND DIAGNOSTIC USE THEREOF

(71) Applicant: COSMO TECHNOLOGIES LTD., Dublin (IE)

(72) Inventors: Luigi Moro, Cairate (IT); Mauro Severino Ajani, Milan (IT); Roberto Villa, Lecco (IT); Giuseppe Celasco, Genoa (IT); Alessandro Repici, Turin (IT)

(73) Assignee: COSMO TECHNOLOGIES LTD., Dublin (IE)

( * ) Notice: Subject to any disclaimer, the term of this patent is extended or adjusted under 35 U.S.C. 154(b) by 233 days.

This patent is subject to a terminal disclaimer.

(21) Appl. No.: 15/061,232

(22) Filed: Mar. 4, 2016

(65) Prior Publication Data

US 2016/0184460 A1   Jun. 30, 2016

Related U.S. Application Data

(63) Continuation of application No. 13/932,321, filed on Jul. 1, 2013, now Pat. No. 9,402,922, which is a continuation of application No. 13/602,875, filed on Sep. 4, 2012, now Pat. No. 8,545,811, which is a continuation-in-part of application No. PCT/IB2011/050881, filed on Mar. 2, 2011.

(60) Provisional application No. 61/327,557, filed on Apr. 23, 2010.

(30) Foreign Application Priority Data

Mar. 4, 2010   (IT) .............................. MI2010A0345

(51) Int. Cl.

| A61K 49/00 | (2006.01) |
| A61K 9/20 | (2006.01) |
| A61K 9/28 | (2006.01) |
| A61B 1/31 | (2006.01) |
| A61B 5/00 | (2006.01) |
| A61M 31/00 | (2006.01) |
| A61B 1/04 | (2006.01) |
| A61B 1/273 | (2006.01) |

(52) U.S. Cl.
CPC .............. *A61K 49/006* (2013.01); *A61B 1/31* (2013.01); *A61B 5/0084* (2013.01); *A61K 9/2054* (2013.01); *A61K 9/2059* (2013.01); *A61K 9/2846* (2013.01); *A61K 49/003* (2013.01); *A61K 49/0073* (2013.01); *A61K 49/0089* (2013.01); *A61M 31/005* (2013.01); *A61B 1/041* (2013.01); *A61B 1/273* (2013.01)

(58) Field of Classification Search
None
See application file for complete search history.

(56) References Cited

U.S. PATENT DOCUMENTS

| 3,361,632 | A | 1/1968 | Ross et al. |
| 7,410,651 | B2 | 8/2008 | Villa et al. |
| 7,410,652 | B2 | 8/2008 | Villa et al. |
| 7,431,943 | B1 | 10/2008 | Villa et al. |
| 8,029,823 | B2 | 10/2011 | Villa et al. |
| 2003/0055341 | A1 | 3/2003 | Banerjee |
| 2004/0258759 | A1 | 12/2004 | Suslick et al. |
| 2007/0077202 | A1 | 4/2007 | Yamamoto |
| 2007/0116757 | A1 | 5/2007 | Rariy et al. |
| 2012/0021052 | A1 | 1/2012 | Villa et al. |
| 2012/0021053 | A1 | 1/2012 | Villa et al. |
| 2012/0213850 | A1 | 8/2012 | Villa et al. |
| 2012/0220559 | A1 | 8/2012 | Villa et al. |

FOREIGN PATENT DOCUMENTS

| WO | 93/08847 A1 | 5/1993 |
| WO | 00/76478 A1 | 12/2000 |
| WO | 00/76481 A1 | 12/2000 |
| WO | 03/026621 A2 | 4/2003 |

OTHER PUBLICATIONS

Danese, S. et al., "An Open Label Trial with Methylene Blue Orally Administered Tablets (MB MMX®) in Patients with Long Standing Ulcerative Colitis," IRCCS Institute Clinico Humanitas, Rozzano—Milan, Italy, POSTER, presented in Amersterdam a UEG Week, Oct. 22-24, 2012, 1 page.

Repici, A. et al., "Diagnostic Accuracy of MMX-MB Panchromocolonoscopy in Pit Pattern Assessment and Characterization of Neoplastic and Non-Neoplastic Colonic Lesions (Preliminary Data)," POSTER, presented in Amersterdam a UEG Week, Oct. 22-24, 2012, 1 page.

Repici, A. et al., "Diagnostic Accuracy of MB-MMX® Panchromocolonoscopy in Pit Pattern Assessment, and Characterization of Neoplastic and Non-Neoplastic Colonic Lesions (Preliminary Data)," POSTER, Instituto Clinico Humanitas, Bologna, Italy, Mar. 20-23, 2013, 1 page.

Repici, A. et al., "Polyp Detection Rate After Single Oral Dose of Methylene Blue MMX Modified Release Tablets Administered to Subjects Undergoing Outpatient Colonoscopy," Presentation, Digestive Disease Week (DDW) 2013, Instituto Clinico Humanitas, Orange County Convention Center, Orlando, FL, May 18-21, 2013, 30 pages.

Danese, Silvio, et al., Poster entitled "Methylene Blue Orally Administered Tablets/MB MMX®) Is Effective in Detecting Intraepithelial Dysplasia In Patients with Long Standing Ulcerative Colitis," ECCO Vienna 2013 Poster, P194, Instituto Clinico Humanitas, one page, presented Feb. 2013.

(Continued)

*Primary Examiner* — Jake M Vu
(74) *Attorney, Agent, or Firm* — Rothwell, Figg, Ernst & Manbeck, P.C.

(57) ABSTRACT

The present application discloses solid compositions for the oral administration of dyes, and diagnostic use thereof. Preferably, such diagnostic use is aimed at the diagnostic evaluation of the gastrointestinal tract.

27 Claims, 3 Drawing Sheets
(2 of 3 Drawing Sheet(s) Filed in Color)

(56) References Cited

OTHER PUBLICATIONS

Boyles. S., "Polyp-Finding Skill is Key to Colonoscopy Success, Study Show Importance of a Doctor's High Polyp-Detection Rate," Colorectal Cancer Health Center, Tools & Resources, WebMD Health News, Reviewed by Laura J. Martin, MD, May 12, 2010, 2 pages.
Cooper, G.S. et al., "The Polyp Detection Rate of Colonoscopy: A National Study of Medicare Beneficiaries," American Journal of Medicine, Dec. 2005, vol. 118, No. 12, p. 1413.
Repici, A. et al., "Methylene Blue MMX® Tablets for Chromoendoscopy, Safety Tolerability and Bioavailability in Healthy Volunteers," Contemporary Clinical Trials (2011), Article in Press, © 2011 Elsevier Inc., 8 pages.
"Variation in Polyp Detection Rates at Screening Colonoscopy," Science Daily, Jun. 29, 2009, 2 pages.
Van Rijn, J.C. et al., "Polyp Miss Rate Determined by Tandem Colonoscopy: A Systematic Review," The American Journal of Gastroenterology (2006), vol. 101, pp. 343-350, 1 page, Abstract only.
PCT International Search Report, dated Jun. 14, 2011, International Appln No. PCT/IB2011/050881, International Filing Date: Feb. 3, 2011, Applicant: Cosmo Technologies Ltd., 6 pages.
Italian Search Report, IO 13386, Appln No. IT MI2010A000345, dated Mar. 4, 2010, Applicant: Cosmo Technologies Ltd., 10 pages.
Yoshida, T. et al. , "Clinical Study of Total Colonoscopic Examination Using Oral Administration of Methylene-Blue Capsule," Journal of the Japan Society of Coloproctology, 1993, vol. 46, pp. 410-415.
Yanbe, T. et al., "Study of Intestinal Metaplapasia of the Stomach by Indirect Dye Scattering Method," Gastroenterological Endoscopy, 1978, vol. 70, No. 8, pp. 714-724.
Official Notice of Rejection (with English translation) dated Aug. 26, 2014, corresponding JP Application No. 2012-555529, 6 pages.
Official Action (with English translation) dated Oct. 6, 2014, corresponding Russian Application No. 2012142192/15 (067906), Filing Date: Mar. 2, 2011, Applicants: Cosmo Technologies, Inc., 11 pages.
BEESWAX (http://en.wikipedia.org/wiki/Beeswax (downloaded on Mar. 19, 2013)).
Breyer et al. "Does methylene blue detect intestinal metaplasia in Barrett's esophagus? Gastrointest Endosc. Apr. 2003:57(4):pp. 505-509."
Repici, A. et al., "Effect of Oral Administration of Methylene Blue MMX® Tablets on Double-Stranded DNA Damage Assessed by γH2AX Analysis of Colon Biopsy Samples—A Single Center, Open Label, Safety, Phase II Study," Abstract (to be presented at DDW 2015), May 16-19, 2015, 1 page.
Repici, A. et al., "In vitro evaluation of DNA damage in human colonic epithelial cell lines exposed to Methylene blue and white light," poster, presented from Sep. 12-16, 2013 at the United European Gastroenterology Week (UEGW) in Berlin, Germany, and from Mar. 19-22, 2014 at FISMAD in Naples, Italy, 1 page.
Mitooka, H. et al., "Minute Flat Depressed Neoplastic Lesions of the Colon Detected by Contrast Chromoscopy Using an Indigo Carmine Capsule," Gastointestinal Endoscopy, May 1, 1995, vol. 41, No. 5, pp. 453-459, © 1995 by the American Society for Gastrointestinal Endoscopy.
Parra-Blanco, A. et al., Colonoscopy With an Indigo Carmine Capsule: A Randomized Controlled Trial, Gastroenterology, vol. 130, Jul. 22, 2006, p. A187, XP-002599122, Abstract, 1 page.

SOLID COMPOSITION FOR THE ORAL ADMINISTRATION OF DYES AND DIAGNOSTIC USE THEREOF

CROSS-REFERENCE TO RELATED APPLICATIONS

The present application is a continuation of U.S. patent application Ser. No. 13/932,321 filed on Jul. 1, 2013, which in turn is a continuation of U.S. patent application Ser. No. 13/602,875 filed on Sep. 4, 2012, now U.S. Pat. No. 8,545,811, which in turn is a continuation-in-part of International Patent Application No. PCT/IB2011/050881 filed on Mar. 2, 2011, which in turn claims priority to U.S. Provisional Patent Application Ser. No. 61/327,557 filed on Apr. 23, 2010 and to Italian Patent Application No. MI2010A000345 filed on Mar. 4, 2010. Each of these applications is incorporated herein in its entirety.

PRIOR ART

The endoscopy is an exceptionally important diagnostic technique for the diagnosis of inflammatory, ulcerative and neoplastic pathologies of the gastrointestinal tract.

Actually, the endoscopy allows observing—from inside the lumen—the state of preservation and development of the mucosa that covers the gastrointestinal cavity, as well as the surface spraying thereof, the presence of deformations and/or ulcerations.

More and more powerful and sophisticated endoscope probes have enabled to improve this technique considerably; the progress of the used materials also allowed improving performance in terms of illumination and resolution power.

More recently there has been an improvement of the conventional diagnostic-therapeutic aspects due to the use of image magnification and vital dyes, useful for locally developing a contrasting colour capable of amplifying the resolution diagnostic power of the conventional technique. The use of dyes in endoscopy lead to coining the term "chromoendoscopy" for describing this diagnostic procedure, particularly useful for identifying suspicious areas for degenerative characteristics.

The use of colouring is generally adopted after completing the endoscopic analysis during the step of withdrawing the endoscopic probe, and after accurately cleaning the mucosa tract to be examined; currently, the dye is applied to the mucosa by spraying a small volume of a solution averagely concentrated with dye, using a catheter or capillary pipe directly inserted into the cavity of the endoscopic probe.

The diffusion of the dye and absorption thereof by the vital cells markedly differentiates the cells with normal vitality from those in the advanced replication stage, for example characteristic of neoplastic cells.

The dyes usually used are mainly, but not exclusively, the following: methylene blue, congo red, carmine indigo, and/or toluidine blue.

Methylene blue and toluidine blue are uniformly absorbed by the whole intestinal mucosa, while, in case of an inflammatory process, absorption thereof by the mucosal cells tends to reduce as the phlogosis worsens. Due to this characteristic, the two dyes are also useful in the step of remission of the inflammatory processes and in the differential diagnosis between pseudopolyps and true polyps. Also carmine indigo has a similar action, finding application in the long duration inflammatory forms and with the aim of highlighting carpet lesions, which can contain tumoral forms, which are difficult to detect with the conventional endoscopy in absence of contrasting colour.

Within the procedure for applying the dye, it should be observed that use thereof reveals several practical problems that are difficult to resolve due to the considerable application difficulty. First and foremost the pharmacy of the institute where the endoscopy is performed should be capable of preparing solutions with concentrations generally comprised between 0.1% and 1% of the dye; then, the endoscopic probe should be provided with a channel for inserting the capillary catheter which carries the solution up to the point of application; then the dye should be dispensed uniformly so as to cover the mucosal surface subject of the evaluation. The need for the simultaneous presence of these precise conditions contributes to the difficulty of executing the chromoendoscopy procedure, which is exclusively carried out by the best diagnostic centres up to date, with extensive defections by hospitals and nursing homes specialized in gastroenterology.

Furthermore, it should be taken into account that the use of a solution to be locally sprayed on the mucosal wall does not entirely solve the problem regarding forms still latent, in that too small to be detected, as well as the degenerative processes of the digestive system.

Thus, there arises the need of providing a simple and safe use of a dye in diagnostic endoscopies, through a suitable means of administration also capable of guaranteeing a homogeneous and complete distribution for an ideal effect of the dye in the area in question.

Now, it has been surprisingly discovered that a solid composition for oral administration allows formulating one, or more, dyes which can thus reach the desired site providing the contrasting image required for endoscopic diagnostic evaluation.

BRIEF DESCRIPTION OF THE FIGURES

The patent or application file contains at least one drawing executed in color. Copies of this patent or patent application publication with color drawing(s) will be provided by the Office upon request and payment of the necessary fee. As the color drawings are being filed electronically via EFS-Web, only one set of the drawings is submitted.

DESCRIPTION

Figure 1:
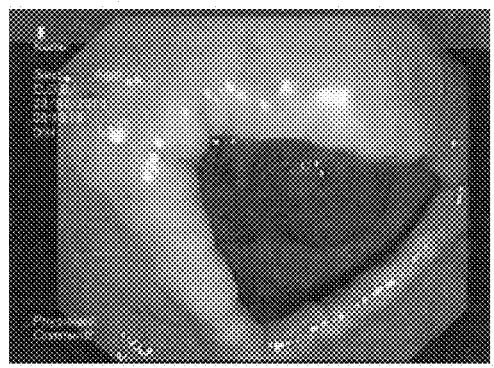
FIG. 1 shows a colon endoscopic image, obtained during the endoscopy of a patient who has taken the composition of the invention within the 24 hours preceding the endoscopy. This figure shows a non-pathologic, non-coloured endoscopic view.
Figure 2:
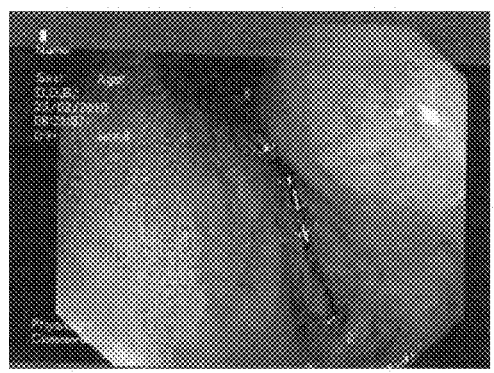
FIG. 2 shows a colon endoscopic image, obtained during the endoscopy of a patient who has taken the composition of the invention within the 24 hours preceding the endoscopy. The endoscopic view is characterized by an excellent visualization of the details of the mucosa and in particular of the pattern of crypts, which are thus clear due to the enhancement and reinforcement action of the dye which, deposited homogeneously, markedly highlights the details of the mucosa that would not be noticeable to the naked eye.
Figure 3:
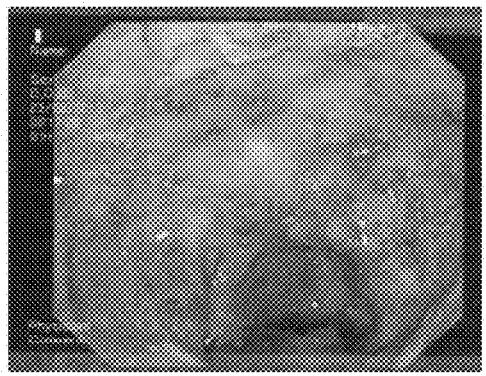
FIG. 3 shows a colon endoscopic image, obtained during the endoscopy of a patient who has taken the composition of the invention within the 24 hours preceding the endoscopy. This view shows that the action of the homogeneously distributed dye allows a clear distinction between the pathologic areas (red) and the non-pathologic areas (lighter). Such distinction would be less marked and clear without the colouring contrast whose action shows an accurate definition of the details of the mucosa and thus an accurate distinction between pathologic and non-pathologic areas in a clearer manner with respect to the endoscopic vision without the dye.
Figure 4:
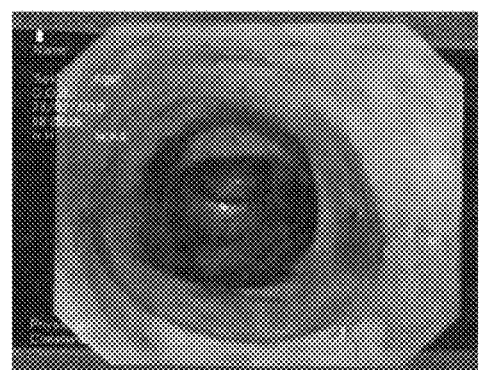
FIG. 4 shows a colon endoscopic image, obtained during the endoscopy of a patient who has taken the composition of the invention within the 24 hours preceding the endoscopy. This view shows that the action of the homogeneously distributed dye allows a clear distinction between the pathologic areas (red) and the non-pathologic areas (lighter). Such distinction would be less marked and clear without the colouring contrast whose action shows an accurate definition of the details of the mucosa and thus an accurate distinction between pathologic and non-pathologic areas in a clearer manner with respect to the endoscopic vision without the dye.

Thus, the present invention is aimed at providing a solid composition for oral administration containing at least one dye suitable for the preparation and evaluation of the endoscopic diagnostic analysis, and at least one physiologically acceptable excipient.

Physiologically acceptable excipients according to the invention are preferably excipients useful for reaching a mass identifiable uniquely, in terms of quality and quantity, and which can be easily administered through the oral cavity.

In particular, the composition of the invention is intended for oral uptake, before being subjected to the endoscopic diagnostic analysis, during or at the end of the procedure for preparing such analysis.

Thus, an object of the present invention is represented by a solid composition, for oral administration, containing at least one dye in association with at least one physiologically acceptable excipient, intended for allowing early local identification of pathologic forms at the gastrointestinal mucosa level, preferably precancerous forms or mucosal areas with high inflammation rate.

The composition of the present invention can be instant-release or controlled-release type, preferably of the controlled release type capable of selectively carrying the dye in the regions subject of the analysis, thus preventing dispersion thereof into areas not subject of the analysis.

The expression "instant-release" is used to indicate a composition capable of disintegrating quickly and dissolving in the gastric cavity, simultaneously releasing the entire dye contained therein.

The instant-release composition of the invention preferably comprises at least one dye in association with physiologically acceptable excipients, technologically indispensable to guarantee the quick disintegration and dissolution of the form in the gastric cavity; more preferably, are used the so-called super disintegrants, i.e. polymeric substances capable of swelling on contact with aqueous fluids and triggering a hydrodynamic tension within the pharmaceutical form which leads to the breakage thereof into fragments with the ensuing considerable increase of the surface/volume ratio and, thus, to a more rapid dissolution of the dye/s contained in the administration form.

Suitable super disintegrants are preferably selected from among modified starches, modified celluloses, polymers or cross-linked copolymers (such as, for example, cross-linked polyvinylpyrrolidone) or mixtures thereof.

The instant-release composition of the invention may also comprise an outer coating, preferably selected from among polymers and copolymers of the acrylic or methacrylic acid, alkyl or hydroxyalkyl cellulose derivatives or mixtures thereof.

The possible presence of such an outer coating is useful for avoiding the coloration of the mucosa of the mouth and/or of the throat during the uptake and swallowing by the patient.

The expression "controlled release" of the invention is used to indicate a composition capable of releasing the dye in a selective site-time manner, i.e. progressive in the areas of interest. Thus, such expression comprises the "rapid, delayed or modified" release definition.

The technology suitable for the formulation of controlled release composition of the invention can be selected from among the matrix technologies and the reservoir diffusion technologies known in the sector.

Preferably the controlled release solid oral composition of the invention is formulated according to the multimatrix technology commercially known under the trade name MMX®, described in the international patent applications WO00/76481 and WO00/76478, incorporated herein by reference.

According to a preferred embodiment of the invention, the controlled release solid oral composition comprises at least one dye and a multimatrix structure containing:

a) a matrix which consists of lipophilic compounds with melting point below 90° C., and optionally amphiphilic compounds, in which at least one dye is at least partly incorporated;

b) an outer hydrophilic matrix in which the lipophilic matrix, and optionally the amphiphilic matrix are dispersed;

c) optionally other physiologically acceptable excipients;

d) optional gastro-resistant coating.

According to a further embodiment, the composition containing at least one dye comprises:

a) a matrix which consists of lipophilic compounds with melting point below 90° C. and amphiphilic compounds in which said at least one dye is at least partly incorporated;

b) an outer hydrophilic matrix in which the lipophilic/amphiphilic matrix is dispersed;

c) optionally other physiologically acceptable excipients;

d) optional gastro-resistant coating.

According to another embodiment, the composition containing at least one dye comprises:

a) a matrix which consists of lipophilic compounds with melting point below 90° C., in which said at least one dye is at least partly incorporated;

b) an outer matrix which consists of hydrophilic compounds and optionally amphiphilic compounds, in which the lipophilic matrix, is dispersed;

c) optionally other physiologically acceptable excipients;

d) optionally a gastro-resistant coating.

Suitable lipophilic compounds in the present invention are preferably selected from among saturated, unsaturated or hydrogenated long chain alcohols, saturated or unsaturated or hydrogenated fatty acids, salts thereof, esters or amides, mono-, di- or triglycerides of fatty acids, polyethoxylated derivatives thereof, waxes, ceramides, cholesterol, cholesterol derivatives or mixtures thereof.

Suitable amphiphilic compounds in the present invention are then preferably selected from among polar lipids of type I or II (lecithin, phosphatidylcholine, phosphatidylethanolamine or a mixture thereof), ceramides, glycol alkyl ethers (such as for example, diethylene glycol monomethyl ether), alkyl sulfate or sulfosuccinate salts or mixtures thereof.

Suitable hydrophilic compounds in the present invention are preferably compounds forming hydrogel (i.e. compounds which form hydrogel on contact with aqueous solvents), more preferably selected from among polymers or copolymers of the acrylic or methacrylic acid, alkyl vinylpolymers, alkyl celluloses, hydroxyalkyl celluloses, carboxyalkyl cellulose, modified or plurisubstituted celluloses, polysaccharides, dextrins, pectins, starches, complex starches and starch derivatives, alginic acid, synthetic rubber, natural rubber, polyalcohols or mixtures thereof.

Suitable gastro-resistant coating according to the invention is preferably selected from among polymers of the acrylic or methacrylic acid, copolymers of the acrylic or methacrylic acid, cellulose derivatives (such as for example cellulose acetate phthalate) hydroxybutyrate-based polymers, shellac or mixtures thereof. Such gastro-resistant coatings of the invention can also be combined with plasticisers, opacifiers, dyes or mixtures thereof.

While the oral administration of instant-release solid pharmaceutical forms allows obtaining a coloration of the first portion of the digestive tract, such as esophagus or stomach, the administration of controlled release compositions of the invention actually allows releasing the dye contained in the composition precisely starting from the gastrointestinal segment intended to be subjected to endoscopic evaluation.

Preferably the composition of the present invention is formulated in form of tablet, capsules, granules, microgranules or pellets. The capsule form according to the invention may in turn contain granules, microgranules or pellets.

More preferably, the composition of the invention may be formulated in form of gastro-resistant tablet or in form of a capsule containing granules, microgranules or gastro-resistant pellets.

Furthermore, the composition of the invention may be formulated in a double layer form, preferably a double layer tablet.

More precisely, instant-release compositions to be administered a few minutes before carrying out the endoscopy analysis using a glass of aqueous liquid are preferable for gastroscopy.

The aqueous liquid is used for facilitating the dissolution of the composition, thus forming—in loco—a coloured solution that allows the dye to homogeneously reach the mucosa which covers the digestive cavity, and to be absorbed or not by the cells of the mucosa covering the stomach.

In case of gastroscopic analysis, the composition of the invention is thus preferably in form of instant-release tablet or capsule.

The same target may be attained in the small or large intestine, due to the use of forms of controlled or targeted release oral administration of the dye; in particular, a composition coated with a thin film of controlled release gastro-resistant polymers is preferred for an environmental pH of about 5 for the small intestine.

In case of endoscopic analysis on the small intestine, the composition of the invention is thus preferably in form of controlled release capsule or tablet, with the presence of a gastro-resistant coating more preferably selected from among mixtures of acrylic and methacrylic copolymers of type A (Eudragit L, or RL, for example).

Even in case of colon endoscopy, it is preferable to use forms of oral administration in solid oral form, coated with gastro-resistant substances, preferably tablet or capsule.

Such gastro-resistant substances are preferably selected from among acrylic and methacrylic copolymers of type A, type B (such as for example those commercially known under the trade name Eudragit S or RS), and/or mixtures based on cellulose acetate phthalate, insoluble in an acid environment which become soluble when the pH is neutralized and acquires a value of about 7. A similar event also occurs when the intestinal transit leads the cud to pass through terminal ileum or through the ileocecal valve. Obviously, in the latter case, considering the fact that the cud takes at least 3-5 hours to complete the transit in the small intestine and an undetermined period of time, ranging from a few minutes to a few hours, for the gastric emptying, the administration of the dye composition should be carried out suitably in advance with respect to the endoscopic analysis, generally for a period comprised between 4-24 hours, so as to allow the dissolution of the dye in situ, the formation of a concentrated solution within the colon lumen due to the intestinal fluid present therein, and the diffusion of the dye on the mucosa for a period of time in which the endoscopic probe is introduced into the intestinal cavity.

In order to allow a homogeneous coloration of the luminal membrane of all colon regions, from the ileocecal area to the ascending, transverse, descending, sigmoid and rectal colon, the release of the dye should not be instantaneous but progressive and in line with the advancement of the composition.

Given that the transit time of the colon tract is once again very variable, but estimated at least 8-16 hours, it is clear that a controlled release composition with the dye being released in vitro in about 6-8 hours constitutes the best system to allow a homogeneous coloration of the entire membrane to be analysed endoscopically and, thus, to obtain the best result in terms of diagnostic evaluation.

Useful dyes according to the present invention are preferably selected from among congo red, carmine indigo, methylene blue, toluidine blue or mixtures thereof. However, according to the invention also other biocompatible dye substances can be used, as long as they are provided with a toxicity profile that does not represent an obstacle to oral systemic administration thereof.

Therefore, the amount of dye that can be used for maximising the structural contrast of the mucosal cells depends:
on the inherent capacity of the dye to induce the coloration of the vital cells,
on the period of time that this coloration should be kept in contact with the cells and
on the massive presence of the liquid for washing the mucosa swallowed during the step of preparing the colonoscopy.

Actually, such parameters may vary the amount of dye from a few milligrams to a few grams of substance, divided into one or more solid oral compositions to be swallowed before or during the step of preparing the endoscopic procedure, or at the end of the procedure.

Preferably, the solid oral composition of the invention comprises at least one dye in an amount comprised between 10 mg (0.01 g) and 1500 mg (1.5 g), per single composition, more preferably between 50 mg (0.05 g) and 1200 mg (1.2 g) per single composition.

Said at least one dye according to the invention may also be comprised in an amount between 2 mg (0.002 g) and 1000 mg (1 g), more preferably between 10 mg (0.01 g) and 500 mg (0.5 g) per single composition.

Said at least one dye according to the invention may also be comprised in an amount between 20 mg (0.02 g) and 500 mg (0.5 g), even more preferably between 25 mg (0.025 g) and 400 mg (0.4 g), per single composition.

According to a preferred embodiment said at least one dye is contained in the solid composition of the invention in an amount equivalent to about 25 mg (0.025 g).

According to a further embodiment said at least one dye is contained in the solid composition of the invention in an amount equivalent to about 50 mg (0.05 g).

According to another embodiment said at least one dye is contained in the solid composition of the invention in an amount equivalent to about 200 mg (0.2 g).

According to a preferred embodiment of the present invention in case of gastroscopy the administration is provided for about 30 minutes before the execution of one or more compositions of the invention, preferably instant-release tablet or capsule.

According to a further embodiment of the present invention, in case of endoscopy of the small intestine there is provided for the administration of one or more compositions of the invention, preferably a controlled release tablet protected by a gastro-resistant coating to prevent early dispersion of the dye in the gastric area not intended to be subjected to the endoscopic evaluation.

According to a further preferred embodiment of the present invention, in case of colonoscopy there is provided for the administration of one or more compositions of the invention, preferably a controlled release tablet so as to prevent the dye from being dispersed into areas of the digestive tract not intended to be subjected to colonoscopy, such as for example the stomach, duodena and jejunum.

For the preparation of controlled release compositions, one or more dyes are preferably formulated alongside substances capable of imparting progressive or massive or controlled or prolonged dissolution properties to the formulation; in addition, the formulation is coated with substances capable of dissolving solely upon reaching a specific pH, generally comprised between 5 and 7, typical of the section subject of the intestinal endoscopic evaluation.

Upon reaching the intestinal section of interest, characterised by a specific pH value at which the gastro-protective coating starts dissolving, it is important that the dissolution of the dye be controlled in terms of speed so as to ensure that it occurs within the time indispensable to the intestinal transit, generally comprised between 4 and 24 hours. Various formulation technologies can be used according to the invention for such purpose.

As mentioned previously, the main and known technologies for obtaining a colon release, such as the use of reservoir systems or diffusion or hydrophilic matrix structures, can be applied for preparing the controlled release composition of the invention; the multi-matrix technology which exploits a sequence of hydrophilic, lipophilic and amphiphilic matrices for obtaining a result as described above is used in a preferable application of the invention. In a typical application of this multimatrix technology, the dye/s is/are first mixed or granulated with the material capable of forming a lipophilic matrix, in the presence of one or more amphiphilic substances with surfactant properties, and lastly this matrix of powders, at any degree of aggregation, is inserted into a dominant structure formed by polymers or copolymers of the hydrophilic type, also known as hydrogels, in the anhydrous state or with low residue moisture value.

Alternatively, still according to a typical application of this technology, the dye/s should be first mixed or granulated with the material capable of forming a lipophilic matrix, and after granulation this matrix structure, at any degree of aggregation, is inserted into a dominant structure formed by polymers or copolymers of hydrophilic type in anhydrous state or with low level of residue humidity in the presence of one or more amphiphilic substances with surfactant properties and subsequently the final mixture is subjected to compression.

A gastro-protective coating film, capable of preventing the dissolution of the tablet in a strongly acid environment, is lastly applied to the surface of the compositions.

Upon swallowing, such a multimatrix coated composition is protected from contact with gastric and intestinal acids up to reaching an environment with suitable pH, preferably greater than 5 or 7, where the gastro-protective coating is solubilised and where the dissolution programme—which will lead it to progressively distribute the dye inserted in the formulation simultaneously with the advancement within the digestive cavity—starts.

Furthermore, an object of the present invention is the abovementioned solid composition for oral administration for diagnostic purpose, preferably in the endoscopic diagnostic evaluation of inflammatory, ulcerative dysplastic, pre-neoplastic and neoplastic pathologies of the gastrointestinal tract, more preferably cancerous or precancerous forms, polyps, pseudopolyps or different inflammatory pathologies of the gastrointestinal tract.

The composition of the present invention is generally applied for oral administration during the preparatory stage for the gastro-intestinal endoscopic analysis in a single solution or in two or more periods of administration. A typical applied administration pattern provides that the administration of the composition, preferably tablet, occurs at the end of the preparatory or cleaning stage of the intestinal mucosa, generally carried out through the uptake of purgatives or polyglycolic laxative substances, or during the preparation procedure, which usually lasts a few hours.

A further administration pattern provides that the administration of the composition of the invention, preferably a tablet, occurs before the previously mentioned preparatory or cleaning stage or that said administration partly occurs before and partly during such preparatory or cleaning step.

Lastly, an object of the present invention is a method for performing endoscopic evaluations of the gastrointestinal tract, comprising the administration, possibly repeated, of the abovementioned composition to be preferably carried out within the day prior to the endoscopy (i.e. within the preceding 24 hours: preparatory stage), such evaluation being aimed at the diagnosis of inflammatory, ulcerative pre-neoplastic, dysplastic or neoplastic pathologies of the gastrointestinal tract, more preferably cancerous or precancerous forms, polyps, pseudopolyps or different inflammatory pathologies of the gastrointestinal tract.

According to a preferred embodiment, the administration of the solid composition of the invention occurs, once or repeated over time, before, simultaneously and/or after the uptake of the preparation/cleaning composition preceding the endoscopic analysis (for example, but not exclusively, using the drug available in the market by the name Moviprep®).

The expression cleaning composition mentioned above is used to indicate the previously mentioned saline, polyglycolic or laxative solution which is commonly used for cleaning and washing the intestinal mucosa before the endoscopic analysis, during the preparatory stage within the preceding 24 hours.

According to a more preferred embodiment of the invention, the solid composition is taken by the subject intending to carry out the endoscopic evaluation of the colon in two administrations where one dose is taken before the washing composition as described above and the subsequent dose is taken after or during the uptake of the washing composition as described previously. According to such embodiment each dose can be constituted by one, or more, solid compositions of the invention, preferably one or more tablets with unitary content corresponding to a fraction of the entire dose to be administered.

The examples below are meant for clarifying the invention, without entailing any restrictions whatsoever with respect thereto.

EXAMPLES

Example 1: Instant-Release Coated Tablet for Endoscopy

| Description | UOM | Amt. per tablet |
|---|---|---|
| Components | | |
| Methylene blue | mg | 50.0 |
| Lecithin | mg | 3.0 |
| Stearic acid | mg | 6.0 |
| Mannitol | mg | 120.0 |
| Microcrystalline cellulose | mg | 50.0 |
| Hydroxypropyl cellulose | mg | 13.0 |
| Sodium starch glycolate | mg | 4.0 |
| Colloidal hydrated silica | mg | 2.0 |
| Magnesium stearate | mg | 2.0 |
| Coating | | |
| Methacrylic acid copolymer type A (Eudragit L) | mg | 12.0 |
| Triethyl citrate | mg | 1.2 |
| talc | mg | 5.8 |
| Titanium dioxide | mg | 3.0 |

The production process provides for mixing the dye, lecithin, stearic acid and mannitol up to obtaining a homogeneous mixture. Then microcrystalline cellulose, hydroxypropyl cellulose, sodium starch glycolate, colloidal silica are added to the mixture and mixed once again. After adding magnesium stearate, the mixture is compressed up to obtaining 250 mg tablets. The tablets are then arranged in a tablet mixer and coated with a methacrylate-based gastro-resistant film and containing triethyl citrate as plasticiser in addition to the titanium dioxide dye and talc, an anti-stick substance. The tablets thus obtained are subjected to a dissolution test in an acid environment for two hours, where they reveal to be resistant to the dyeing substance. The tablets yield to the dye within a few minutes upon introduction into a neutral pH environment.

Example 2: Instant-Release Coated Tablet for Endoscopy

| Description | UOM | Amt. per tablet |
|---|---|---|
| Components | | |
| Methylene blue | mg | 600.0 |
| Lecithin | mg | 5.0 |
| Stearic acid | mg | 10.0 |
| Mannitol | mg | 340.0 |
| Microcrystalline cellulose | mg | 123.0 |
| Sodium starch glycolate | mg | 30.0 |
| Colloidal hydrated silica | mg | 20.0 |
| Magnesium stearate | mg | 12.0 |
| Coating | | |
| Methacrylic acid copolymer type A (Eudragit L) | mg | 30.0 |
| Triethyl citrate | mg | 3.0 |
| talc | mg | 15.0 |
| Titanium dioxide | mg | 7.0 |

The tablet was obtained through the same process indicated in example 1.

The dissolution test applied to the tablet of example 2 allowed establishing the substantial non-dissolution of the tablets in an acid environment with pH at 1 and the subsequent dissolution in vitro of the dye when moved to a 6.8 pH.

Example 3: Instant-Release Coated Tablet for Endoscopy

| Description | UOM | Amt. per tablet |
|---|---|---|
| Components | | |
| Methylene blue | mg | 1200.0 |
| Lecithin | mg | 10.0 |
| Stearic acid | mg | 20.0 |
| Mannitol | mg | 200.0 |
| Hydroxypropyl cellulose | Mg | 50.0 |
| Microcrystalline cellulose | mg | 20.0 |
| Sodium starch glycolate | mg | 50.0 |
| Colloidal hydrated silica | mg | 30.0 |
| Magnesium stearate | mg | 20.0 |
| Coating | | |
| Methacrylic acid copolymer type A (Eudragit L) | mg | 40.0 |
| Triethyl citrate | mg | 4.0 |
| talc | mg | 20.0 |
| Titanium dioxide | mg | 9.0 |

The tablet was obtained through the same process indicated in example 1.

Even in this case, the dissolution test applied to the tablets allowed establishing the substantial non-dissolution of the tablets in an acid environment with pH at 1 and the subsequent dissolution in vitro of the dye when moved to a 6.8 pH, mimetic value of the intestinal pH.

Example 4: Intestinal Release Coated Tablet for Endoscopy

| Description | UOM | Amt. per tablet |
|---|---|---|
| Components | | |
| Carmine indigo | mg | 50.0 |
| Lecithin | mg | 3.0 |
| Stearic acid | mg | 6.0 |
| Mannitol | mg | 120.0 |
| Microcrystalline cellulose | mg | 40.0 |
| Hydroxypropyl cellulose | mg | 23.0 |
| Sodium starch glycolate | mg | 4.0 |
| Colloidal hydrated silica | mg | 2.0 |
| Magnesium stearate | mg | 2.0 |
| Coating | | |
| Methacrylic acid copolymer type A (Eudragit L) | mg | 6.0 |
| Methacrylic acid copolymer type B (Eudragit S) | mg | 6.0 |
| Triethyl citrate | mg | 1.2 |
| talc | mg | 5.8 |
| Titanium dioxide | mg | 3.0 |

The applied process provides for mixing the dye with the lecithin surfactant, stearic acid, mannitol and half of the required amount of magnesium stearate. After compacting the mixture followed by granulation, cellulose, sodium starch glycolate, colloidal silica and the remaining magnesium stearate are added and then, after further mixing, the final compression is carried out up to obtaining 250 mg tablets. The tablet is then coated with a mixture of methacrylic copolymers of type A and B, so as to extend the resistance to the dissolution in vitro up to a pH≥7, characteristic of the ileocecal and colon environment.

Example 5: Intestinal Release Coated Tablet for Endoscopy

| Description | UOM | Amt. per tablet |
|---|---|---|
| Components | | |
| Carmine indigo | mg | 500.0 |
| Lecithin | mg | 3.0 |
| Stearic acid | mg | 6.0 |
| Mannitol | mg | 120.0 |
| Microcrystalline cellulose | mg | 50.0 |
| Hydroxyethylcellulose | mg | 13.0 |
| Sodium starch glycolate | mg | 4.0 |
| Colloidal hydrated silica | mg | 2.0 |
| Magnesium stearate | mg | 2.0 |
| Coating | | |
| Methacrylic acid copolymer type A (Eudragit L) | mg | 15.0 |
| Methacrylic acid copolymer type B (Eudragit S) | mg | 15.0 |
| Triethyl citrate | mg | 3.0 |
| talc | mg | 15.0 |
| Titanium dioxide | mg | 7.0 |

The applied process provides for mixing the dye with the lecithin surfactant, stearic acid and mannitol. After homogeneously dispersing the dye in the mixture, cellulose, sodium starch glycolate, colloidal silica and the lubricant magnesium stearate are added and then, after further mixing, the final compression is carried out up to obtaining 700 mg tablets. The nuclei are then subjected to coating using a mixture of methacrylic copolymers of type A and B alongside other auxiliary substances: the tablets resist to the dissolution in vitro in an acid environment and they dissolve at a pH≥7, characteristic of the ileocecal and colon environment.

Example 6: Intestinal Release Coated Tablet for Endoscopy

| Description | UOM | Amt. per tablet |
|---|---|---|
| Components | | |
| Methylene blue | mg | 50.0 |
| Lecithin | mg | 3.0 |
| Stearic acid | mg | 6.0 |
| Mannitol | mg | 120.0 |
| Microcrystalline cellulose | mg | 35.0 |
| Hydroxypropyl methylcellulose | Mg | 28.0 |
| Sodium starch glycolate | mg | 4.0 |
| Colloidal hydrated silica | mg | 2.0 |
| Magnesium stearate | mg | 2.0 |
| Coating | | |
| Methacrylic acid copolymer type A (Eudragit L) | mg | 6.0 |
| Methacrylic acid copolymer type B (Eudragit S) | mg | 6.0 |
| Triethyl citrate | mg | 1.2 |
| talc | mg | 5.8 |
| Titanium dioxide | mg | 3.0 |

The preparation process provides for mixing the dye with lecithin, stearic acid and microcrystalline cellulose, compaction thereof into wafers followed by dry granulation, mixing with the remaining components of the nucleus and the final compression to the weight of 250 mg/tab. The coating uses methacrylic derivatives as base and an alcohol solvent as application phase.

The tablets thus obtained were subjected to dissolution test in vitro, revealing a good resistance to the acid environment and a progressive transfer of the dye in the neutral environment with pH at 7.2.

Example 7: A Colon Controlled Release Tablet

| Description | UOM | Amt. per tablet |
|---|---|---|
| Components | | |
| Methylene blue | mg | 200.0 |
| Lecithin | mg | 5.0 |
| Stearic acid | mg | 14.0 |
| Methylhydroxypropyl cellulose | mg | 180.0 |
| Mannitol | mg | 140.0 |
| Microcrystalline cellulose | mg | 140.0 |
| talc | mg | 10.0 |
| Colloidal hydrated silica | mg | 5.0 |
| Magnesium stearate | mg | 6.0 |
| Coating | | |
| Methacrylic acid copolymer type A (Eudragit L) | mg | 16.0 |
| Methacrylic acid copolymer type B (Eudragit S) | mg | 16.0 |
| Triethyl citrate | mg | 6.4 |

| Description | UOM | Amt. per tablet |
|---|---|---|
| talc | mg | 15.6 |
| Titanium dioxide | mg | 6.0 |

The composition is obtained through advance mixing and granulation of the dye, the lecithin as amphiphilic component, the stearic acid as component of the lipophilic matrix, mannitol and part of the magnesium stearate; after screening the granules obtained preliminarily, the remaining components and in particular cellulose, capable of producing the hydrophilic matrix structure are added. The final pharmaceutical form, obtained by compressing the mixture of powders and granules, weighing about 700 mg, is subjected to coating with a mixture of copolymers of methacrylic derivatives of type A and B, supported by a plasticiser, triethyl citrate, by a dye pigment, titanium dioxide, and by an anti-stick agent, such as talc, using ethylic alcohol as solvent.

The tablet thus obtained revealed in vitro a substantial non-dissolution at acid pH for 2 hours and a progressive dissolution for about 6 hours in a simulated intestinal medium with 7.2 pH.

Example 8: Colon Endoscope Experimental Test

The same tablet of example 7 was used for carrying out some colon endoscopies in a human being with extremely positive results. A single tablet was administered to a subject about 12 hours before carrying out the endoscopy, during the intestinal preparation step, followed by the uptake of about further 500 ml of water. The time that elapsed between the uptake of the tablet and the execution of the endoscopy, about 12 hours, was useful to allow the tablet to reach the intestinal colon region and start the progressive and slow transfer of the dye which, due to the solubilisation in the liquid present therein, allowed the homogeneous, intense and persistent coloration of the intestinal mucosa. Actually, after the administration the colon environment revealed noticeable areas of coloration, allowing a considerable contrast between the pathologic areas and the normal mucosa which covers the ascending, transverse, descending, sigmoid and rectal colon regions.

FIGS. 1-4 show four (4) colon endoscopic images, obtained during the endoscopy of a patient who has taken the composition of the invention within the 24 hours preceding the endoscopy. The images clearly show how only some zones of the colon area of the patient are coloured, while the others are normal. This shows how after the uptake of the composition of the invention, the dye highlights solely the pathologic zones of the examined colon area (see FIGS. 2, 3-4), and not the zones to be considered non-pathologic (see FIG. 1).

Thus, this shows the efficiency of the indicated composition when determining the elective coloration of the pathologic intestinal areas and, by contrast, a non-pathologic area which, consequently, is free of coloration.

Example 8-Bis: Bioavailability Study

The same tablet was used for a bioavailability and pharmacokinetic study in which the profile of blood absorption and urinary elimination of the dye administered to healthy volunteers during a clinical study of Phase I was determined; the pharmacokinetic parameters were compared with those obtained after intravenous administration of a 100 mg dose of dye and they were as follows:

| | T max | $C_{max}$ | $AUC_{(o-t)}$ |
|---|---|---|---|
| 100 mg i.v. vial | 0.10 hrs | 2066 ng/ml | 11858 ng/ml * h |
| 200 mg tablets | 16 hrs | 1662 ng/ml | 32941 ng/ml * h. |

Figure 5:
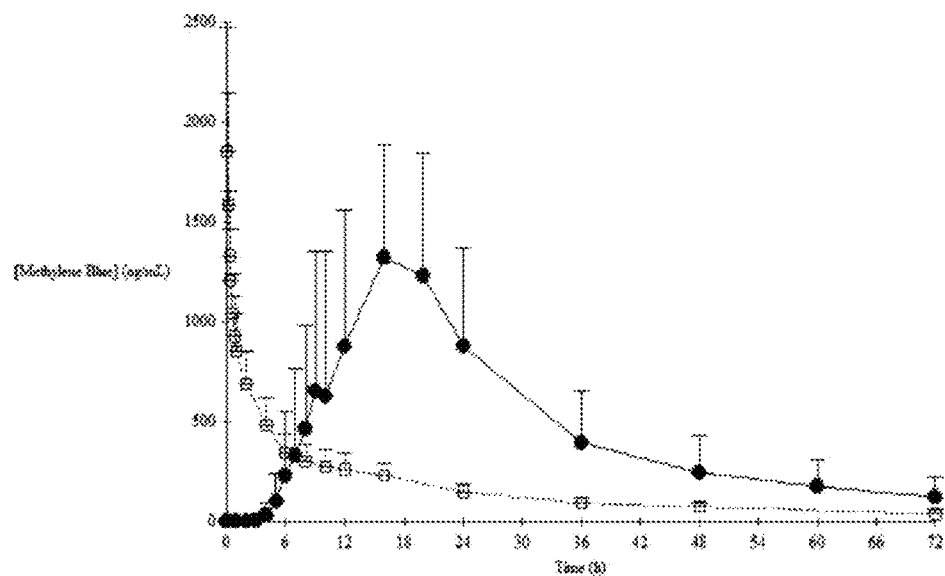
FIG. 5 shows that the tablet absorption profile (circles) is markedly different from that of the vial (squares) and it can be classified as a typical absorption profile of a controlled release formulation.

The tablets absorption profile is markedly different from that of the vial and it can be classified as a typical absorption profile of a controlled release formulation, also as shown in FIG. 5.

Example 9: Colon Endoscope Experimental Test

Using the tablet of example 7, there was carried out an endoscopy test of the colon by administering two tablets to a subject awaiting colonoscopy, according to the specified uptake method, i.e. by taking the first dye tablet at the end of the preparatory stage and the second tablet about 6 hours before carrying out the endoscopy evaluation. The tablets were administered with abundant water, so as to efficiently support the in situ dissolution of the tablets.

Also in this case, the coloration was homogeneous and well marked, allowing carrying out the test in optimal conditions for diagnostic purposes.

Example 9-Bis: Bioavailability Study

The same tablet was used for a bioavailability and pharmacokinetic study in which the profile of blood absorption and urinary elimination of the dye administered to healthy volunteers during a clinical of Phase I was determined; the pharmacokinetic parameters measured after the administration of two 200 mg tablets are the following:

| T max | $C_{max}$ | $AUC_{(0-t)}$ |
|---|---|---|
| 16 hrs | 1636 ng/ml | 38080 ng/ml * h. |

Figure 6:
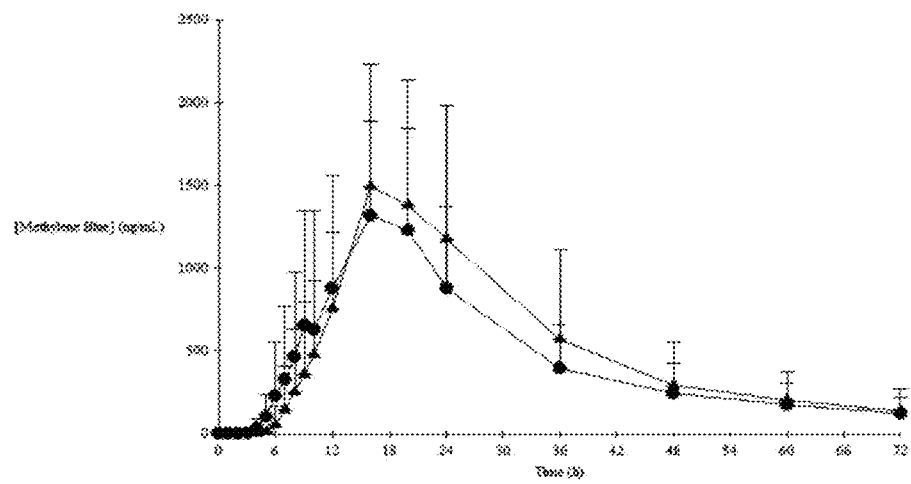
FIG. 6 shows that the tablet absorption profile for the 400 mg tablet (circles) is very similar to the profile obtained with the 200 mg tablet (dots) and, once again, it can be classified as a typical absorption profile of a controlled release formulation, also as outlined by the chart B below, where the chart with the dot refers to the 200 mg dose while the one with the triangle refers to the 400 mg one.

The tablets absorption profile is very similar to the profile obtained with the 200 mg tablet and, once again, it can be classified as a typical absorption profile of a controlled release formulation, also as shown in FIG. 6, where the chart with the dot refers to the 200 mg dose while the one with the triangle refers to the 400 mg one.

Example 10: Colon Release Coated Tablet

| Description | UOM | Amt. per tablet |
|---|---|---|
| Components | | |
| Toluidine blue | mg | 400.0 |
| Carmine indigo | mg | 100.0 |
| Lecithin | mg | 5.0 |
| Stearic acid | mg | 10.0 |
| Mannitol | mg | 30.0 |
| Methylhydroxypropyl cellulose | mg | 95.0 |
| Microcrystalline cellulose | mg | 10.0 |
| Sodium starch glycolate | mg | 25.0 |
| Colloidal hydrated silica | mg | 15.0 |

| Description | UOM | Amt. per tablet |
| --- | --- | --- |
| Magnesium stearate | mg | 10.0 |
| Coating | | |
| Methacrylic acid copolymer type A (Eudragit L) | mg | 20.0 |
| Methacrylic acid copolymer type B (Eudragit S) | mg | 20.0 |
| Triethyl citrate | mg | 4.0 |
| talc | mg | 20.0 |
| Titanium dioxide | mg | 9.0 |

The preparation process provides for the formation of a granulate containing toluidine blue, lecithin, stearic acid, mannitol and part of the magnesium stearate; after compaction and reduction into granules through screening, the second Carmine indigo dye, cellulose, sodium starch glycolate, colloidal silica and the remaining magnesium stearate lubricant are added. After homogenization, the mixture is compressed to 700 mg and subsequently subjected to coating as described in example 7, using the two copolymers of the methacrylic acid and the other functional excipients.

The tablet thus obtained resists to dissolution in vitro in buffers with pH<2 and allows a progressive release of the dye substances in buffers with pH>7.

Example 11: Gastric Immediate Release Coated Tablet

| Description | UOM | Amt. per tablet |
| --- | --- | --- |
| Components | | |
| Congo red | mg | 50.0 |
| Lecithin | mg | 3.0 |
| Stearic acid | mg | 6.0 |
| Mannitol | mg | 120.0 |
| Microcrystalline cellulose | mg | 63.0 |
| Sodium starch glycolate | mg | 4.0 |
| Colloidal hydrated silica | mg | 2.0 |
| Magnesium stearate | mg | 2.0 |
| Coating | | |
| Methyl hydroxypropyl cellulose | mg | 12.0 |
| Polyethylene glycol 6000 | mg | 1.2 |
| talc | mg | 6.0 |
| Titanium dioxide | mg | 3.8 |

Obtained through the direct compression method, followed by coating in an aqueous solvent. The tablet dissolves rapidly in vitro within a few minutes, according to the specifications required by the regulatory authorities for immediate release tablets.

The tablet thus obtained can be used for endoscopic evaluations of the gastroduodenal sector for highlighting local pathologic growths which can be related to dysplastic or neoplastic processes still at the initial stage.

Example 12: Double Layer Tablet

| Description | UOM | Amt. per tablet |
| --- | --- | --- |
| Layer 1 | | |
| Congo red | mg | 100.0 |
| Dioctyl sulfosuccinate | mg | 5.0 |
| Stearic acid | mg | 10.0 |
| Mannitol | mg | 100.0 |
| Microcrystalline cellulose | mg | 100.0 |
| Sodium starch glycolate | mg | 20.0 |
| Colloidal hydrated silica | mg | 10.0 |
| Magnesium stearate | mg | 5.0 |
| Layer 2 | | |
| Methylene blue | mg | 100.0 |
| Lecithin | mg | 7.0 |
| Stearic acid | mg | 10.0 |
| Methylhydroxypropyl cellulose | mg | 100.0 |
| Mannitol | mg | 80.0 |
| Microcrystalline cellulose | mg | 40.0 |
| talc | mg | 50.0 |
| Colloidal hydrated silica | mg | 7.0 |
| Magnesium stearate | mg | 6.0 |
| Coating | | |
| Methyl hydroxypropyl cellulose | mg | 12.0 |
| Polyethylene glycol 6000 | mg | 1.2 |
| talc | mg | 6.0 |
| Titanium dioxide | mg | 3.8 |

The process provides for mixing the components of layer 1 and compression thereof, followed by the compression of a mixture of powders and granules obtained from a previous compaction of some components of the layer 2, precisely the dye, lecithin, stearic acid, the microcrystalline cellulose and mannitol with half of the magnesium stearate, with the remaining co-formulants.

The tablet, weighing about 850 mg, has two differently coloured distinct layers formulated for differentially releasing the dye both in the gastric sector and in the subsequent intestinal sector.

Example 13: A Colon Controlled Release Tablet

| Description | UOM | Amt. per tablet |
| --- | --- | --- |
| Methylene blue | mg | 25.0 |
| Lecithin | mg | 3.0 |
| Stearic acid | mg | 10.0 |
| Methylhydroxypropyl cellulose | mg | 90.0 |
| Mannitol | mg | 121.0 |
| Microcrystalline cellulose | mg | 140.0 |
| talc | mg | 3.0 |
| Colloidal hydrated silica | mg | 5.0 |
| Magnesium stearate | mg | 3.0 |
| Coating | | |
| Methacrylic acid copolymer type A (Eudragit L) | mg | 8.0 |
| Methacrylic acid copolymer type B (Eudragit S) | mg | 8.0 |
| Triethyl citrate | mg | 3.2 |
| talc | mg | 7.8 |
| Titanium dioxide | mg | 3.0 |

The composition is obtained through advance mixing of the dye, the lecithin as amphiphilic component, the stearic acid as component of the lipophilic matrix, a thirds of the quantity of mannitol; then the remaining components were added and in particular the celluloses, capable of producing the hydrophilic matrix structure up to completion of the formula. The final pharmaceutical form, obtained by compressing the mixture of powders and granules, unitary weighing of about 320 mg, is subjected to coating with a mixture of copolymers of methacrylic derivatives of type A and B, supported by a plasticiser, triethyl citrate, by a dye pigment, titanium dioxide, by a small quantity of the dye, methylene blue, and by an anti-stick agent, such as talc, using ethylic alcohol as solvent.

The tablet thus obtained revealed in vitro a substantial non-dissolution at acid pH for 2 hours and a progressive dissolution in a simulated intestinal medium with 7.2 pH with a release of about 45% within the first 4 hours and a release part more than 80% at the eighth hour.

The invention claimed is:

1. A method of endoscopic evaluation of the colon in a subject, the method comprising:
   endoscopically evaluating the colon of the subject, wherein prior to conducting the endoscopic evaluation the subject was orally administered an effective amount of at least one solid composition in the form of a tablet, the tablet comprises:
   a tablet core comprising:
      methylene blue,
      stearic acid,
      lecithin,
      methylhydroxypropylcellulose, and
      optionally other physiologically acceptable excipients; and
   a gastro-resistant coating on the tablet, wherein the coating comprises methacrylic acid copolymer Type A and methacrylic acid copolymer Type B.

2. The method of claim 1, wherein the solid composition is a controlled release composition.

3. The method of claim 1, wherein the oral administration of at the least one solid composition to the subject is carried out once or repeatedly within a 24 hour period preceding the endoscopic evaluation.

4. The method of claim 3, wherein the oral administration of the at least one solid composition to the subject is carried out within a 4 hour to 24 hour period preceding the endoscopic evaluation.

5. The method of claim 3, wherein the oral administration of the at least one solid composition to the subject is fractioned into two or more doses.

6. The method of claim 1, wherein the solid composition comprises at least one dye in an amount ranging between 10 mg and 1500 mg per dose.

7. The method of claim 1, wherein the solid composition comprises at least one dye in an amount ranging between 2 mg and 1000 mg per dose.

8. The method of claim 1, wherein the solid composition comprises at least one dye in an amount ranging between 20 mg and 500 mg per dose.

9. The method of claim 1, wherein the solid composition comprises at least one dye in an amount selected from the group consisting of an amount of about 25 mg per dose, an amount of about 50 mg per dose, and an amount of about 200 mg per dose.

10. A method of enhancing the endoscopic evaluation of the colon in a subject undergoing colonoscopy, the method comprising:
    performing a colonoscopy, wherein prior to conducting the colonoscopy the subject was orally administered an effective amount of at least one solid composition in the form of a tablet, the tablet comprises:
    a tablet core comprising:
       methylene blue,
       stearic acid,
       lecithin,
       methylhydroxypropylcellulose, and
       optionally other physiologically acceptable excipients; and
    a gastro-resistant coating on the tablet, wherein the coating comprises methacrylic acid copolymer Type A and methacrylic acid copolymer Type B.

11. The method of claim 10, wherein the solid composition is a controlled release composition.

12. The method of claim 10, wherein the oral administration of the at least one solid composition to the subject is carried out once or repeatedly within a 24 hour period preceding the colonoscopy.

13. The method of claim 12, wherein the oral administration of the at least one solid composition to the subject is carried out within a 4 hour to 24 hour period preceding the colonoscopy.

14. The method of claim 12, wherein the oral administration of the at least one solid composition to the subject is fractioned into two or more doses.

15. The method of claim 10, wherein the solid composition comprises at least one dye in an amount ranging between 10 mg and 1500 mg per dose.

16. The method of claim 10, wherein the solid composition comprises at least one dye in an amount ranging between 2 mg and 1000 mg per dose.

17. The method of claim 10, wherein the solid composition comprises at least one dye in an amount ranging between 20 mg and 500 mg per dose.

18. The method of claim 10, wherein the solid composition comprises at least one dye in an amount selected from the group consisting of an amount of about 25 mg per dose, an amount of about 50 mg per dose, and an amount of about 200 mg per dose.

19. A method of colouring the gastrointestinal tract in a subject undergoing an endoscopic evaluation of the gastrointestinal tract, the method comprising orally administering to the subject prior to the endoscopic evaluation at least one solid composition in an amount effective for colouring the gastrointestinal tract of the subject, wherein the at least one solid composition is in the form of a tablet, the tablet comprises:
    a tablet core comprising:
       methylene blue,
       stearic acid,
       lecithin,
       methylhydroxypropylcellulose, and
       optionally other physiologically acceptable excipients; and
    a gastro-resistant coating on the tablet, wherein the coating comprises methacrylic acid copolymer Type A and methacrylic acid copolymer Type B.

20. The method of claim 19, wherein the solid composition is a controlled release composition.

21. The method of claim 19, wherein the oral administration of the at least one solid composition to the subject is carried out once or repeatedly within a 24 hour period preceding the endoscopic evaluation.

22. The method of claim 21, wherein the oral administration of the at least one solid composition to the subject is carried out within a 4 hour to 24 hour period preceding the endoscopic evaluation.

23. The method of claim 21, wherein the oral administration of the at least one solid composition to the subject is fractioned into two or more doses.

24. The method of claim 19, wherein the solid composition comprises at least one dye in an amount ranging between 10 mg and 1500 mg per dose.

25. The method of claim 19, wherein the solid composition comprises at least one dye in an amount ranging between 2 mg and 1000 mg per dose.

26. The method of claim 19, wherein the solid composition comprises at least one dye in an amount ranging between 20 mg and 500 mg per dose.

27. The method of claim 19, wherein the solid composition comprises at least one dye in an amount selected from the group consisting of an amount of about 25 mg per dose, an amount of about 50 mg per dose, and an amount of about 200 mg per dose.

* * * * *